United States Patent
Breyta et al.

(10) Patent No.: US 11,795,292 B2
(45) Date of Patent: Oct. 24, 2023

(54) MEDIA RECYCLING AND SANITIZATION

(71) Applicant: International Business Machines Corporation, Armonk, NY (US)

(72) Inventors: Gregory Breyta, San Jose, CA (US); Robert David Allen, Golden, CO (US)

(73) Assignee: International Business Machines Corporation, Armonk, NY (US)

(*) Notice: Subject to any disclaimer, the term of this patent is extended or adjusted under 35 U.S.C. 154(b) by 57 days.

(21) Appl. No.: 17/525,799

(22) Filed: Nov. 12, 2021

(65) Prior Publication Data

US 2022/0169825 A1  Jun. 2, 2022

Related U.S. Application Data

(60) Provisional application No. 63/120,338, filed on Dec. 2, 2020.

(51) Int. Cl.
| | |
|---|---|
| *C08J 11/28* | (2006.01) |
| *C07C 67/333* | (2006.01) |
| *C22B 7/00* | (2006.01) |
| *B29B 17/02* | (2006.01) |

(52) U.S. Cl.
CPC .............. *C08J 11/28* (2013.01); *B29B 17/02* (2013.01); *C07C 67/333* (2013.01); *C22B 7/006* (2013.01); *B29B 2017/0272* (2013.01); *C08J 2325/06* (2013.01)

(58) Field of Classification Search
USPC .................................. 521/47, 48.5; 528/305
See application file for complete search history.

(56) References Cited

U.S. PATENT DOCUMENTS

| | | | |
|---|---|---|---|
| 3,284,348 A | 11/1966 | Hutton | |
| 3,666,791 A | 5/1972 | Chikawa et al. | |
| 3,668,235 A | 6/1972 | Ichikawa et al. | |
| 3,691,092 A | 9/1972 | Floria | |
| 4,003,880 A | 1/1977 | Sidebotham et al. | |
| 4,003,881 A | 1/1977 | Sidebotham et al. | |
| 4,064,079 A | 12/1977 | Sidebotham et al. | |
| 4,118,187 A | 10/1978 | Sidebotham et al. | |
| 4,137,393 A | 1/1979 | Sidebotham et al. | |
| 4,435,485 A * | 3/1984 | Nakajima | G11B 5/7023 360/134 |
| 4,735,848 A * | 4/1988 | Kondo | G11B 5/7253 427/128 |
| 4,952,435 A * | 8/1990 | Okita | G11B 5/825 427/132 |
| 5,273,830 A * | 12/1993 | Yaguchi | G11B 5/735 |
| 6,191,197 B1 * | 2/2001 | Wang | C08L 53/025 524/483 |
| 7,030,264 B1 | 4/2006 | Inada et al. | |
| 7,211,193 B2 | 5/2007 | Inada et al. | |
| 9,255,194 B2 * | 2/2016 | Allen | C07C 51/09 |
| 9,914,816 B2 | 3/2018 | Allen et al. | |
| 2004/0182782 A1 | 7/2004 | Inada et al. | |
| 2015/0232632 A1 | 8/2015 | Walker | |
| 2017/0218162 A1 | 8/2017 | Walker | |
| 2019/0345306 A1 | 11/2019 | Walker | |

FOREIGN PATENT DOCUMENTS

WO    2021032826 A1   2/2021

* cited by examiner

*Primary Examiner* — Terressa Boykin
(74) *Attorney, Agent, or Firm* — Karen Canaan; CanaanLaw, P.C.

(57) ABSTRACT

Polyester-free magnetic and/or metallic components are obtained from a multicomponent polyester device by reacting the multicomponent polyester device with an amine organocatalyst and/or carboxylic acid salt of same and an alcohol solvent. The reaction recovers (i) the polyester-free magnetic and/or metallic components as solid inert byproducts of the reaction, (ii) the amine organocatalyst and/or carboxylic acid salt of same for reuse, (iii) unreacted alcohol for reuse, and (iv) a polyester monomer product. Where the multicomponent device includes a non-polyester material, such as polystyrene, the polystyrene is fully recovered from the reaction. Where the multicomponent polyester device includes recording media, the reaction process sanitizes the inert byproducts of the recording media, thus scrubbing any personal data from the reacted recording media.

22 Claims, 3 Drawing Sheets

MEDIA RECYCLING AND SANITIZATION

TECHNICAL FIELD

The present invention relates generally to recycling processes and more specifically to a depolymerization process for recycling and sanitizing media products.

BACKGROUND OF THE INVENTION

Recycling of polymers is challenging due to the nature of polymers to not tolerate other material. Foreign, dissimilar polymers, dyes, pigment, dirt, etc., will cause severe degradation of the properties (mechanical, optical, barrier, etc.). Both mechanical recycling and chemical recycling face separate challenges from low quality and from mixed plastic waste.

The problem is further complicated with devices having a plurality of potentially valuable components each with potential to be recycled. A good example of the are items such as radios, computers, and other electronic and mechanical devices comprised of various component materials of different composition. One such device that has presented itself as particularly difficult is magnetic tape that is used for data and media storage. There is a tremendous stockpile of archival and legacy types of media storage such as reel-to-reel, VHS, cassette and 8-track form factors that are or are coming past their lifecycle usefulness and are ending up in landfills. Additionally, there is the problem of destroying and recycling the large amount of archival data storage used in highly proprietary and sensitive industries and government applications.

These include sensitive data on individuals such as social security numbers, financial and other personal information used by banks and governments which are securely stored for protection. Yet another large volume use of magnetic and optical information is videotape used by the movie industry (where there is a desire to prevent pirating) and imaging media used by hospitals where very little is currently recycled. To date, these materials have been difficult or impossible to recycle while they contain valuable components such as silver, expensive magnetic media particles, steel components, and a variety of polymers such as polystyrene and polyesters such as polyethylene terephthalate (PET) and polyethylene naphthalate (PEN).

Chemical recycling of polyester is a method that in principle should work for the digestion of the polyester component of a complex mixture such as described above. However, the ability of recovering the other useful components might be expected to be non-trivial. We demonstrate that this is not the case.

SUMMARY OF THE INVENTION

In one aspect, the present invention relates to a method comprising: reacting a multicomponent device comprising a polyester component and a magnetic and/or metallic component with an amine organocatalyst and/or carboxylic acid salt of same and an alcohol solvent; and recovering (i) the magnetic and/or metallic component as a solid inert by-product of the reaction, (ii) the amine organocatalyst and/or carboxylic acid salt of same for reuse, (iii) unreacted alcohol for reuse, and (iv) a polyester monomer product In another aspect, the present invention relates to a method comprising: reacting a multicomponent media device comprising a polyethylene terephthalate (PET) component, a polystyrene component, and a magnetic and/or metallic component with an amine organocatalyst and/or carboxylic acid salt of same and an alcohol solvent; and recovering (i) magnetic and/or metallic component as solid inert by-products of the reaction, (ii) the amine organocatalyst and/or carboxylic acid salt of same for reuse, (iii) unreacted alcohol solvent for reuse, (iv) bis(2-hydroxyethyl) terephthalate) (BHET), and (v) the polystyrene component.

In a further aspect, the present invention relates to a method comprising: reacting a multicomponent media device comprising a polyethylene naphthalate (PEN) component, a polystyrene component, and a magnetic and/or metallic component with an amine organocatalyst and/or carboxylic acid salt of same and an alcohol solvent; and recovering (i) magnetic and/or metallic component as solid inert by-products of the reaction, (ii) the amine organocatalyst and/or carboxylic acid salt of same for reuse, (iii) unreacted alcohol solvent for reuse, (iv) bis(2-hydroxyethyl) naphthalate (BHEN), and (v) the polystyrene component.

Additional aspects and/or embodiments of the invention will be provided, without limitation, in the detailed description of the invention that is set forth below.

DETAILED DESCRIPTION OF THE INVENTION

Figure 1:
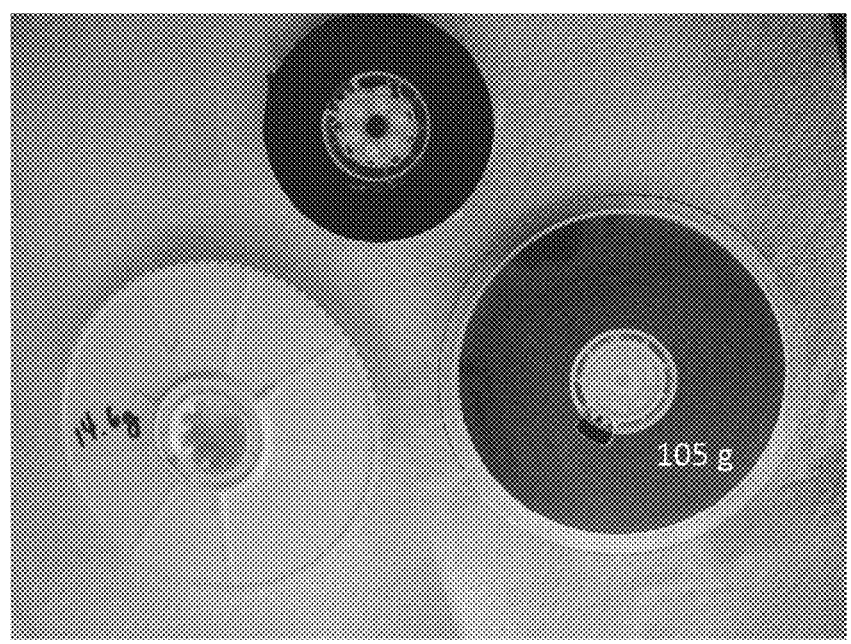
FIG. 1 is a photograph of typical magnetic tape components that may be recycled and sanitized with the VolCat process described herein.

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

As used herein, the term "sanitized" is meant to refer to the scrubbing of data from a recording media product comprising a magnetic component.

As used herein, the term "magnetic and/or metallic component(s)" is meant to refer to magnetic tape, magnetic particles, metallic tape, metallic particles, metal salts, and combinations thereof.

As used herein, the term "multicomponent device" is meant to refer to a device that includes a polyester-based component, a magnetic and/or metallic component, and optionally, a non-polyester-based component. Examples of a multicomponent device includes, without limitation, a cartridge or enclosure containing a spool of magnetic tape, a cartridge or enclosure for recording media, and a reel of film.

Described herein is a volatile catalyst (VolCat) process that when applied to a polyester based storage medium produces multiple product streams, including, without limitation, recycled magnetic and/or metallic components, recycled polystyrene, and a recycled polyester monomer, the latter of which may be used for the subsequent production of a new polyester (of either bottle or textile quality). VolCat is a gentle and highly selective process that depolymerizes the input polyester component allowing the components originally bound to the input polyester to be recovered.

The VolCat chemical recycling process is described in U.S. Pat. No. 9,255,194 B2 to Allen et al. and U.S. Pat. No. 9,914,816 B2 to Allen et al. In one embodiment, the VolCat process depolymerizes polyester with an alcohol solvent and an amine organocatalyst and/or carboxylic acid salt of same in a reactor at a temperature at or higher than the boiling point of the alcohol. In another embodiment, the amine organocatalyst and/or carboxylic acid salt of same has a boiling point at least 50° C. lower than the boiling point of the alcohol and the depolymerization is run at a temperature higher than the boiling point of the alcohol solvent. In a further embodiment, the organocatalyst has a boiling point at least 50° C. lower than the boiling point of the alcohol solvent and the depolymerization is run at a temperature higher than the boiling point of the organocatalyst. In another embodiment, the polyester input and the alcohol solvent are heated to a reaction temperature of about 200-250° C. prior to the introduction of the amine organocatalyst and/or carboxylic salt of same. Reaction products from the VolCat depolymerization are monomeric and/or oligomeric diesters from the polyester as well as recovered organocatalyst and excess alcohol solvent, the former of which is intended for reuse into recycled polyester products and the latter of which may also be reused in subsequent depolymerization reactions.

In another embodiment, the VolCat reaction is carried out in a chemical reactor, which may be a pressure reactor, such as an autoclave or extrusion reactor, or a non-pressurized reactor, such as a round bottom flask. In a further embodiment, the depolymerization reaction, which may be pressurized or non-pressurized, as well as one or more optional purification steps for the monomer product are carried out in batches and/or in a continuous flow process. In another embodiment, a solvent in which the monomer product has limited solubility may be used to purify the depolymerized polyester monomer product, whether obtained in a batch process or though continuous flow. Alcohol and/or water are non-limiting examples of such purification solvents. Where an alcohol is used for the purification, the alcohol may be the unreacted alcohol from the depolymerization reaction or a newly introduced clean alcohol. In a further embodiment, the recovered monomer product obtained from the VolCat reaction may be used to produce a new polymer material.

In another embodiment, the polyester is selected from the group consisting of polyethylene terephthalate (PET), polyethylene naphthalate (PEN), polybutylene terephthalate (PBT), polytrimethylene terephthalate (PTI), polyethylene furanoate (PEF), and combinations thereof. In a further embodiment, the alcohol solvent is a glycol and/or diol solvent. In another embodiment, the alcohol solvent is selected from the group consisting of 1,2-ethanediol (ethylene glycol, EG), 1,3-propanediol (trimethylene glycol), 1,4-butanediol (tetramethylene glycol), 1,5-pentanediol (pentylene glycol), and combinations thereof. In a further embodiment, the amine of the amine organocatalyst and/or carboxylic acid salt of same is a tertiary amine. In another embodiment, the amine organocatalyst and/or carboxylic acid salt of same is selected from the group consisting of triethylamine (TEA), tetramethylethylenediamine (TMEDA), pentamethyldiethylenetriamine (PMDETA), trimethyl triaza cyclononane (TACN), 4-(N,N-dimethylamino)pyridine (DMAP), 1,4-diazabicyclo[2.2.2]octane (DABCO), N-methyl imidazole (NMI), and combinations thereof. In a further embodiment, the amine organocatalyst and/or carboxylic acid salt of same is TEA and/or a carboxylic acid salt of same.

In one embodiment, the polyester input comprises a terephthalate and the recovered depolymerized reaction product comprises a terephthalate ester monomer. In another embodiment, the polyester input comprises PET and the recovered polyester monomer product is bis(2-hydroxyethyl)terephthalate (BHET). In a further embodiment, the polyester input comprises PET, the alcohol is EG, the amine organocatalyst is TEA and/or a carboxylic salt of same, and the recovered reaction products comprise unreacted EG, the TEA, and BHET. In another embodiment, the polyester input comprises a naphthalate and the recovered depolymerized reaction product is a naphthalate ester monomer. In a further embodiment, polyester input comprises PEN and the recovered polyester monomer product is bis(2-hydroxyethyl)naphthalate (BHEN). In another embodiment, the polyester input comprises PEN, the alcohol is EG, the amine organocatalyst is TEA and/or a carboxylic salt of same, and the recovered reaction products comprise unreacted EG, the TEA, and BHEN.

When the VolCat process is used on a multicomponent device comprising a polyester component, such as PET and/or PEN, the VolCat reaction depolymerizes the polyesters in the storage media and dissolves the polyester monomers in the glycol solvent thus releasing as by-products all non-polyester materials from their polyester components, without any polyester contamination.

In one embodiment, the VolCat reaction produces useable recycled products including, without limitation, magnetic and/or metallic components as defined herein, non-polyester polymer materials, and the monomer obtained from the depolymerization of the input polyester (e.g., BHET from PET and/or BHEN from PEN). The monomer obtained from the depolymerization reaction may be used to produce a new polyester material. In another embodiment, the magnetic and metallic components of the multicomponent device may be recovered from the VolCat reaction as reaction products by filtration, magnetic attraction, flocculation, adsorption, chemical means, and combinations thereof. In a further embodiment, non-magnetic metallic materials of the multicomponent may be recovered from the reaction product by screening, filtration, fractionation, and combinations thereof. In another embodiment, non-polyester polymers, such as for example, polystyrene, are readily recovered from the VolCat reaction. As non-polyester polymers are not affected by the selective VolCat depolymerization process, such non-polyester polymers are recoverable as a result of their lack of reactivity and insolubility in the solvent (the latter of which contains the polyester monomer). Polystyrene for example floats and can be skimmed form the surface of the reaction vessel or recovered by another technique, such as screening, filtration, and/or fractionation. All the components of the multicomponent device can thus be easily recovered for recycling while also providing the added benefit of destruction of the data and images contained therein.

Application of the VolCat process to a multicomponent device allows for environmentally sound destruction of sensitive data/information/media while concurrently allowing for the recovery and reuse of all the individual components that make up the multicomponent device without the need to resort to landfills or incineration for disposal purposes. An additional advantage to the application of the VolCat process on multicomponent devices is the sanitization of recording and/or storage media without the need to resort to degaussing, overwriting, shredding, or other mechanical destruction. The following discussion describes the VolCat depolymerization of a magnetic tape-containing media product; however, it is to be understood that a media product containing a metallic component (in addition to or as an alternative to a magnetic component) may also be successfully recovered with the VolCat process.

The following discussion references the depolymerization of a multicomponent device comprising PET and the recovery of BHET; however, it is to be understood that the discussion is exemplary and not limiting and the depolymerization method described herein may be used on a multicomponent device comprising other materials, such as for example, PEN, which produces a BHEN monomer product.

FIG. 1 shows spools containing PET base magnetic tape. The spools contain ~15% polystyrene. The type and size of magnetic particles in the tape are unknown. The spools and tape, together or independently, are suitable inputs for the VolCat depolymerization process.

Figure 2:
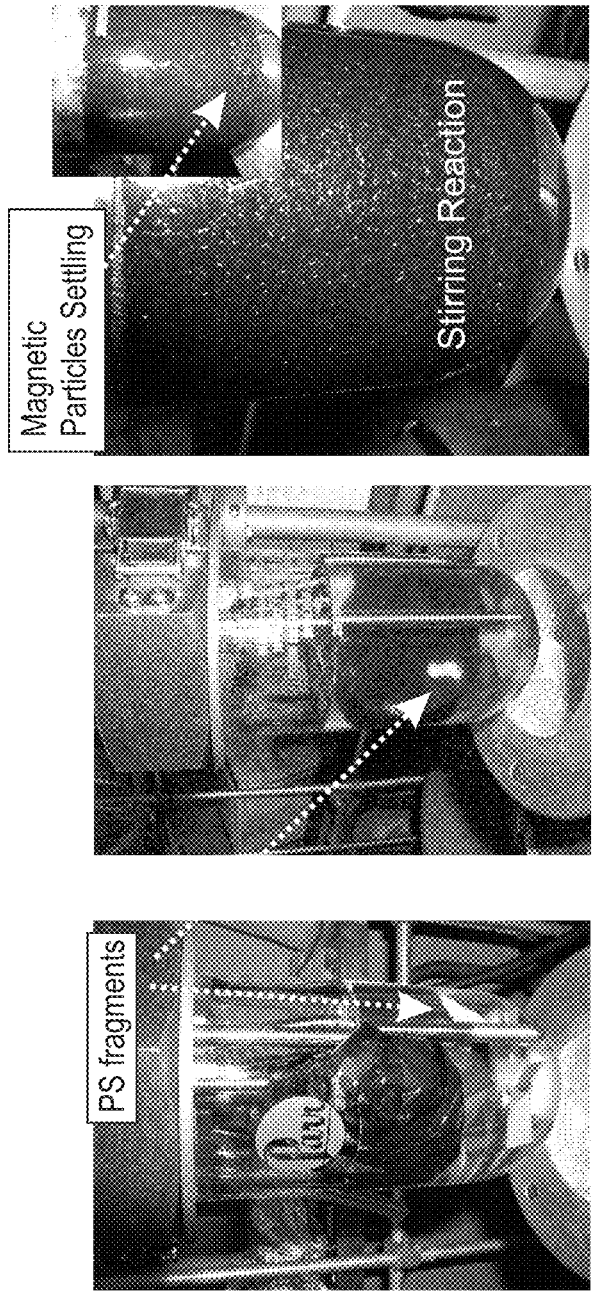
FIG. 2 are photographs showing the VolCat process applied to magnetic tape within a polystyrene spool. The left panel shows the spool containing the magnetic tape within the VolCat reactor with ethylene glycol; the center panel shows the cartridge in the reactor just prior to addition of the triethylamine (TEA) organocatalyst; and the right panel shows the reaction when complete.

FIG. 2 shows the VolCat process applied to a magnetic tape within a polystyrene (PS) spool applied. The left panel shows insertion of ~45 g of a magnetic tape-filled PS spools (type and size of magnetic particles unknown) into a VolCat reactor with EG. The center panel shows the tape-filled spool and cartridge in the VolCat reactor heated to 220° C. prior to addition of the amine organocatalyst TEA. The PS spools have a glass transition temperature ($T_g$) of ~100° C. and a melting temperature ($T_m$) of ~210-249° C. The right panel shows the same tape-filled spool following the completion of the VolCat process while and after stopping stirring. Upon depolymerization of the PET tape, the resulting BHET reaction product is in the EG solution along with TEA. The BHET, TEA, and EG reaction products are recoverable for reuse (Example 1). Not shown is a small neodymium magnet that was inserted into the reaction vessel to capture magnetic particles while in suspension. The inset of FIG. 2 (right panel) shows that the magnetic particles from the tape aggregate settle to the bottom of the still heated reactor when the stirring is stopped (the coalesced PS from the spools is within the opaque solution).

Figure 3:
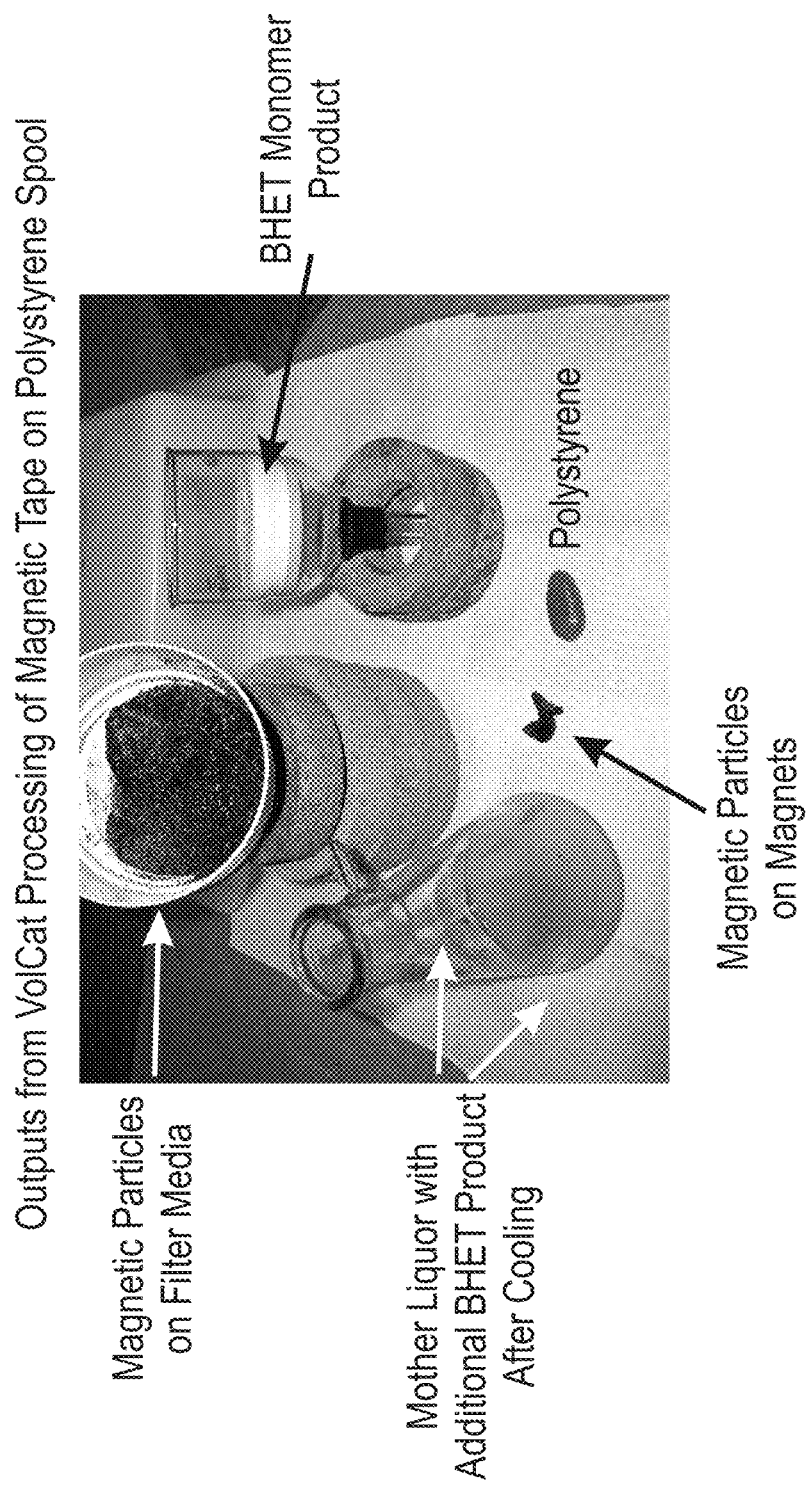
FIG. 3 is a photograph showing the materials recovered from the spooled magnetic tape after the VolCat process of FIG. 2.

FIG. 3 shows the outputs from the VolCat processing of the magnetic tape shown in FIG. 2 after post-reaction processing. Shown are magnetic particles recovered on a neodymium magnet that was suspended in the heated solution prior to filtration. The remaining solid materials are recovered by filtration of the heated reactor output (shown in FIG. 3 on the filter media) and a mass of coalesced PS. After cooling, the filtered reaction BHET monomer product is crystalized and recovered by filtration along with the mother liquor containing unreacted EG, the TEA, and additional BHET. The additional BHET can be further separated from the mother liquid by filtration and the TEA and EG are separated by distillation before or after the reaction is allowed to cool to crystallize the BHET product. Following the distillation, the recovered TEA and EG are available for reuse in another VolCat recycling process.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following Examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be considered. Unless indicated otherwise, parts are parts by weight, and temperature is degrees centigrade. In the Examples that follow, pressure is measured following the heating of the stated components in a sealed reactor and brought to temperature, such pressure readings being typically (but not necessarily) in the range of 50 psig. All components were obtained commercially unless otherwise indicated.

Example 1

Recovery of Spooled Magnetic Tape and Cartridge Materials 45 g of a mixture of the magnetic tape, spool, and cartridge material (roughly of compositional equivalent to an intact magnetic tape carrier) and 250 g of EG were sealed in a 450 mL glass Parr reactor (FIG. 2, left panel) and heated to 220-230° C. (FIG. 2, center panel). 700 mg of TEA was then added and the reaction mixture was heated for 1 hour. The reaction was then cooled to 90° C. (FIG. 2, right panel) and a small neodymium magnet was briefly lowered into the liquid to recover a portion of the magnetic particles that were in suspension. The liquid was then filtered through filter paper to recover the remaining magnetic particles and the polystyrene, the latter of which was recovered as a single coalesced mass. The TEA (bp 89° C.) was mostly separated from the filtered product at this step. The liquid removed during the filtration was first treated with 15 g of activated carbon, then 10 g of AMBERLYST® 15 ion exchange resin (DDP Specialty Electronic Materials, Wilmington, Del., USA) for 30 minutes and then the liquid was filtered through a diatomaceous earth filter aid over filter paper and then allowed to cool. Any remaining traces of TEA were removed during the treatment with the acidic AMBERLYST resin. After cooling, BHET was recovered along with the mother liquor (EG and remaining BHET). All output products are shown in FIG. 3.

We claim:
1. A method comprising:
   reacting a multicomponent device comprising a polyester component and a magnetic and/or metallic component with an amine organocatalyst and/or carboxylic acid salt of same and an alcohol solvent; and
   recovering (i) the magnetic and/or metallic component as a polyester-free solid inert by-product of the reaction,
   (ii) the amine organocatalyst and/or carboxylic acid salt of same for reuse, (iii) unreacted alcohol for reuse, and (iv) a polyester monomer product.

2. The method of claim 1, wherein the polyester monomer product is dissolved in the alcohol solvent and is separated from the solid inert by-products of the reaction.

3. The method of claim 1, wherein the magnetic and/or metallic component is recovered by a technique selected from the group consisting of filtration, magnetism, centrifugation, evaporation, and combinations thereof.

4. The method of claim 1, wherein the magnetic and/or metallic component of the multi-component device comprises recorded media and the recovered polyester-free magnetic and/or metallic component is sanitized of data that was contained within or on the recorded media prior to the reaction of the multicomponent media device with the amine organocatalyst and/or carboxylic acid salt of same and the alcohol solvent.

5. The method of claim 1, wherein the amine of the amine organocatalyst and/or carboxylic acid salt of same is a tertiary amine and the alcohol solvent is a glycol or a diol.

6. The method of claim 1, wherein the amine organocatalyst and/or carboxylic acid salt of same is triethylamine and the alcohol solvent is ethylene glycol.

7. The method of claim 1, wherein multicomponent device comprise a polyethylene terephthalate (PET) component and the recovered polyester monomer product is bis(2-hydroxyethyl)terephthalate (BHET).

8. The method of claim 1, wherein multicomponent device comprises a polyethylene naphthalate (PEN) component and the recovered polyester monomer product is bis(2-hydroxyethyl)naphthalate (BHEN).

9. The method of claim 1, wherein the multicomponent device comprises at least one non-polyester component that is recovered following the reaction of the multicomponent device with the amine organocatalyst and/or carboxylic acid salt of same and the alcohol solvent.

10. The method of claim 9, wherein the non-polyester component is a polystyrene component.

11. A method comprising:
reacting a multicomponent media device comprising a polyethylene terephthalate (PET) component, a polystyrene component, and a magnetic and/or metallic component with an amine organocatalyst and/or carboxylic acid salt of same and an alcohol solvent; and
recovering (i) the magnetic and/or metallic component as a polyester-free solid inert by-products of the reaction, (ii) the amine organocatalyst and/or carboxylic acid salt of same for reuse, (iii) unreacted alcohol solvent for reuse, (iv) bis(2-hydroxyethyl)terephthalate) (BHET), and (v) the polystyrene component.

12. The method of claim 11, wherein the BHET is dissolved in the alcohol solvent and is separated from the solid inert by-products of the reaction.

13. The method of claim 11, wherein the polyester-free magnetic and/or metallic component is recovered by a technique selected from the group consisting of filtration, magnetism, centrifugation, evaporation, and combinations thereof.

14. The method of claim 11, wherein the magnetic and/or metallic component of the multi-component device comprises recorded media and the recovered polyester-free magnetic and/or metallic component is sanitized of data that was contained within or on the recorded media prior to the reaction of the multicomponent media device with the amine organocatalyst and/or carboxylic acid salt of same and the alcohol solvent.

15. The method of claim 11, wherein the amine of the amine organocatalyst and/or carboxylic acid salt of same is tertiary amine and the alcohol solvent is a glycol or a diol.

16. The method of claim 11, where the amine organocatalyst and/or carboxylic acid salt of same is triethylamine and/or carboxylic acid salt of same and the alcohol solvent is ethylene glycol.

17. A method comprising:
reacting a multicomponent media device comprising a polyethylene naphthalate (PEN) component, a polystyrene component, and a magnetic and/or metallic component with an amine organocatalyst and/or carboxylic acid salt of same and an alcohol solvent; and
recovering (i) magnetic and/or metallic component as a polyester-free solid inert by-products of the reaction, (ii) the amine organocatalyst and/or carboxylic acid salt of same for reuse, (iii) unreacted alcohol solvent for reuse, (iv) bis(2-hydroxyethyl)naphthalate (BHEN), and (v) the polystyrene component.

18. The method of claim 17, wherein the BHEN is dissolved in the alcohol solvent and is separated from the solid inert by-products of the reaction.

19. The method of claim 17, wherein the polyester-free magnetic and/or metallic component is recovered by a technique selected from the group consisting of filtration, magnetism, centrifugation, evaporation, and combinations thereof.

20. The method of claim 17, wherein the magnetic and/or metallic component of the multi-component device comprises recorded media and the recovered polyester-free magnetic and/or metallic component is sanitized of data that was contained within or on the recorded media prior to the reaction of the multicomponent media device with the amine organocatalyst and/or carboxylic acid salt of same and the alcohol solvent.

21. The method of claim 17, wherein the amine of the amine organocatalyst and/or carboxylic acid salt of same is tertiary amine and the alcohol solvent is a glycol or a diol.

22. The method of claim 17, where the amine organocatalyst and/or carboxylic acid salt of same is triethylamine and/or carboxylic acid salt of same and the alcohol solvent is ethylene glycol.

\* \* \* \* \*